(12) United States Patent
DeVore

(10) Patent No.: US 9,033,154 B2
(45) Date of Patent: May 19, 2015

(54) INFECTION PREVENTION SYSTEM WITH IV POLE FLUSH AND SWAB CADDY

(71) Applicant: Dovette DeVore, Blaine, MN (US)

(72) Inventor: Dovette DeVore, Blaine, MN (US)

( * ) Notice: Subject to any disclaimer, the term of this patent is extended or adjusted under 35 U.S.C. 154(b) by 301 days.

(21) Appl. No.: 13/630,743

(22) Filed: Sep. 28, 2012

(65) Prior Publication Data

US 2013/0081966 A1 Apr. 4, 2013

Related U.S. Application Data

(60) Provisional application No. 61/542,806, filed on Oct. 4, 2011.

(51) Int. Cl.
| | | |
|---|---|---|
| *B65D 83/10* | (2006.01) | |
| *B65D 69/00* | (2006.01) | |
| *A61B 19/02* | (2006.01) | |
| *A61B 19/00* | (2006.01) | |

(52) U.S. Cl.
CPC ....... *A61B 19/026* (2013.01); *A61B 2019/0209* (2013.01); *A61B 2019/0221* (2013.01); *A61B 2019/0249* (2013.01); *A61B 2019/267* (2013.01)

(58) Field of Classification Search
USPC .................. 206/363, 370, 438, 570, 571, 806
See application file for complete search history.

(56) References Cited

U.S. PATENT DOCUMENTS

| | | | | |
|---|---|---|---|---|
| 3,638,603 | A * | 2/1972 | Conover ........................ | 116/308 |
| 4,795,441 | A * | 1/1989 | Bhatt ............................ | 604/124 |
| 5,055,099 | A * | 10/1991 | Mintz ........................... | 604/6.15 |
| 7,967,137 | B2 * | 6/2011 | Fulbrook et al. ............... | 206/370 |
| 8,083,729 | B2 * | 12/2011 | Colantonio et al. ........... | 604/539 |
| 8,366,679 | B2 * | 2/2013 | Cole et al. ...................... | 604/192 |
| 2003/0097232 | A1 * | 5/2003 | McClendon et al. ......... | 702/114 |
| 2004/0170409 | A1 * | 9/2004 | Faries et al. .................... | 392/470 |
| 2004/0243162 | A1 * | 12/2004 | Wulfman et al. .............. | 606/167 |
| 2008/0283534 | A1 * | 11/2008 | Paz ................................ | 220/528 |
| 2009/0301927 | A1 * | 12/2009 | Fvlbrook et al. .............. | 206/564 |
| 2012/0195769 | A1 * | 8/2012 | Susi ................................. | 417/1 |

* cited by examiner

*Primary Examiner* — Jacob K Ackun

(57) ABSTRACT

A bed-side system for preventing infection that uses a flush and swab caddy attached to an IV pole or other bed-side equipment. By providing convenient and secure storage for pre-filled syringes, alcohol swabs, and other medical supplies, it can improve individual patient care. In an embodiment, the caddy attaches to the IV pole and comprises a locking compartment for pre-filled syringes and an open tray for alcohol swabs and other medical supplies. The syringes may be filled with saline, heparin, or another solution.

8 Claims, 2 Drawing Sheets

INFECTION PREVENTION SYSTEM WITH IV POLE FLUSH AND SWAB CADDY

CROSS-REFERENCES TO RELATED APPLICATIONS

This application claims the benefit of U.S. Provisional Patent Application Ser. No. 61/542,806, entitled "IV Pole Flush and Swab Caddy" filed Oct. 4, 2011, the contents of which is herein incorporated by reference in its entirety.

STATEMENT REGARDING FEDERALLY SPONSORED RESEARCH OR DEVELOPMENT

Not Applicable.

PARTIES TO A JOINT RESEARCH AGREEMENT

Not Applicable

FIELD OF THE INVENTION

The field of the invention is in medical and nursing practices and equipment for direct patient care.

BACKGROUND OF THE INVENTION

Every year patients acquire catheter-related blood stream infections (CRBSI) in the health care setting. These infections are an issue that increase health care costs and negatively affect patient health and can also lead to death. Each health care acquired CRBSI is estimated to cost anywhere from $25,000 to $55,000 on average to treat. As of August 2008, insurance policies no longer pay the costs associated with these infections. Instead, the added costs are incurred by the health care facility or institution. Patients who acquire a CRBSI have an increased risk of death. Systems and methods for reducing infections are needed, and are required for compliance with accrediting agencies.

Proper care and maintenance of Vascular Access Devices (VAD) can reduce the incidence of CRBSI. Having medical supplies close at hand to the patient can aid clinical personnel in providing this proper care and maintenance. Two clinical tasks associated with proper care and maintenance are the cleansing of the VAD injection cap hub prior to all medication administration, and the assessment and flushing of the VAD's. Regular flushes with solutions such as saline, heparin, or other solutions can help prevent central line infections and other complications. Such flushes are important for keeping the IV lines/Vascular Access Devices (VAD) patent by proper assessment and care. FDA regulations require that saline and other solutions (typically in pre-filled syringes) must be locked unless in use; this practice is also a safety measure. But, this regulation poses a problem for busy health care providers. The pre-filled syringes are often locked up in a central area outside the patient rooms, not next to the patient or even in the same room as the patient. In addition, when a patient is taken out of their room to another department for testing, the necessary supplies for VAD assessment and care are not available. If a patient has a life threatening event in another department such as radiology, and they need IV medications immediately in the case of cardiac arrest, they have to wait until the supplies or the crash cart arrives. This increases mortality. The same problem arises with cleansing swabs used to clean the end caps of VAD devices. These swabs are often kept in a "clean stock room" outside the patient's room, or if they are stocked in the patient's room, the supply of swabs often runs out.

To reduce interruptions to patient care that would be caused by clinical staff frequently leaving the room to obtain needed medical supplies, nurses and other health care workers may carry saline flush syringes around in their pocket or they may leave one or more pre-filled syringes in a patient's room unsecured. In addition, because a convenient supply of fresh alcohol swabs for cleaning the end caps of the IV line is often not available, swabs may be re-used, or cleansing of the end caps may not be done at all, which leads to infections for patients. Such practices are violations of regulations established by groups such as the Food and Drug Administration (FDA), the Centers for Disease Control (CDC), and the Joint Commission on Accreditation of Healthcare Organizations (JCAHO).

A bed-side system for infection prevention that provides convenient access to pre-filled medication syringes, alcohol swabs, and other medical supplies would improve health care for patients and help lower health care costs related to infection. A bed-side caddy that can provide secured access to regulated medicinal supplies and open access to other non-regulated supplies is not found in the prior art and would be useful in a bed-side system for infection prevention. By having the bed-side caddy with the locking compartment housing the necessary flushes, clinicians will be more compliant which in turn will create an environment of proactive patient assessment and care.

SUMMARY OF THE INVENTION

The invention provides a bed-side system for preventing infection that uses a flush and swab caddy attached to an IV pole or other bed-side equipment. By providing convenient and secure storage for pre-filled syringes, alcohol swabs, and other medical supplies following FDA and regulating agency guidelines, it can improve individual patient care. In an embodiment, the caddy attaches to the IV pole and comprises a locking compartment for pre-filled syringes and an open tray for cleansing swabs to clean the VAD hub as well as other medical supplies. The syringes may be filled with saline, heparin, or other medications prescribed to the patient by their MD which are best kept near the patient.

If the medication is not a 'stock' flush used per facility policy or protocol, it would need to come from the pharmacy and labeled per patient. It could still be stored within the locking compartment of the caddy on the patient's individual IV pole. One such medication would be Narcan for patients on IV Narcotics. It must be with the patient at all times in case the patient receives an accidental overdose—to reverse the life threatening sedative effects and save the patient's life. Since it is a prescription medication, it is required by FDA to be locked up—often times, it is rubber banded to the patient's IV pole, a practice that is not compliant with FDA guidelines. The bed-side caddy would assist the facility with compliance and patient safety.

In an embodiment, the invention comprises a caddy comprising a non-permeable plastic locking box which attaches to an IV pole or bedside bar in a medical setting using a clamp. The caddy comprises a compartment that locks to store IV flush syringes and medications, and the caddy also comprises an open tray to hold swabs for IV line hub or lumen cleansing/disinfection. This invention enables health care workers to have necessary equipment at hand to facilitate best patient care and save health care workers time. This invention will also decrease the risk of catheter related blood stream infections by facilitating best patient care in regards to infusion.

DETAILED DESCRIPTION OF THE INVENTION

Figure 1:
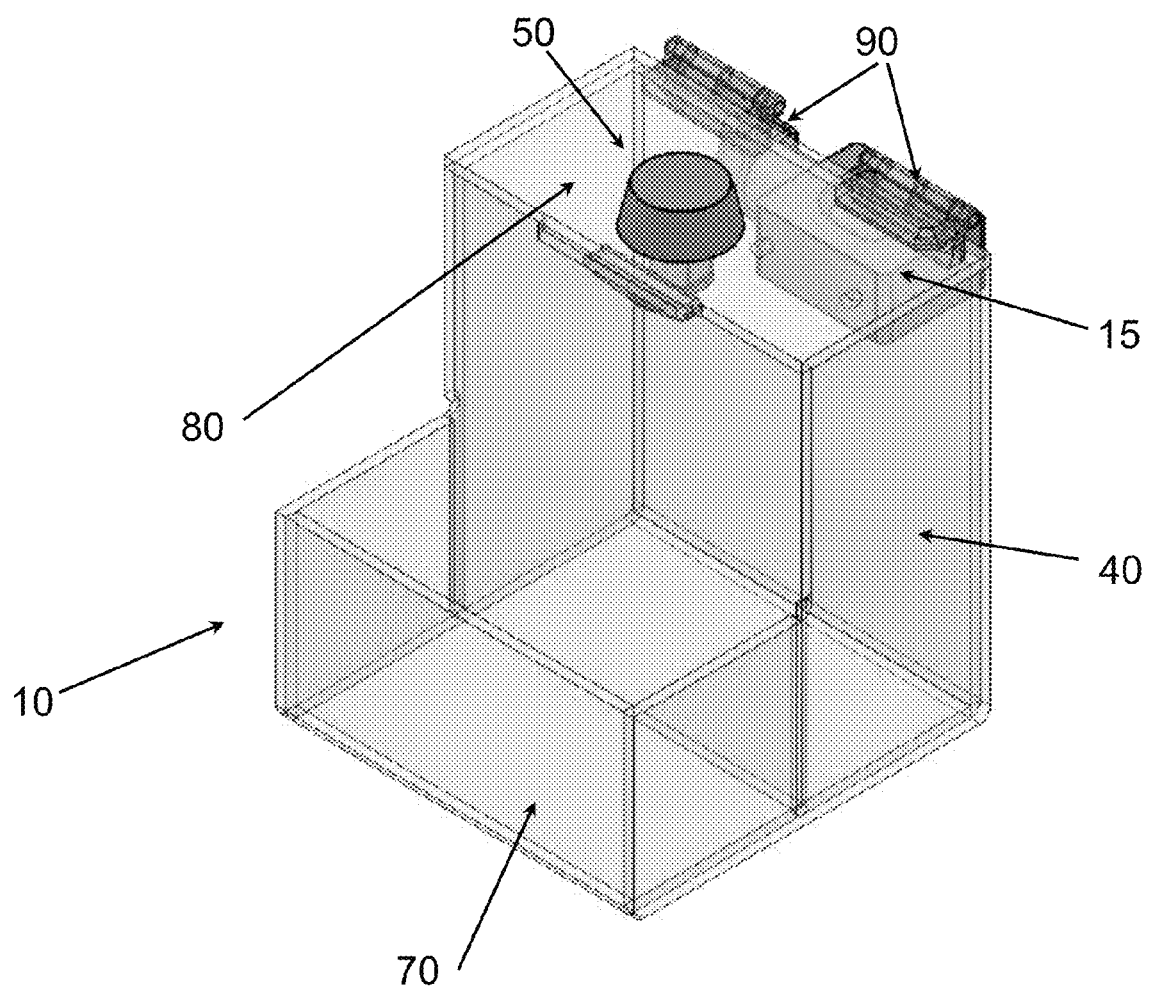
FIG. 1 is a perspective view of an embodiment of the invention

The invention provides a bed-side system for preventing infection that uses a flush and swab caddy attached to an IV pole or other bed-side equipment. By providing convenient and secure storage for pre-filled syringes, medications, prescription items, hub cleansing swabs or swab caps, and other medical supplies, it can improve individual patient care. This invention enables health care workers to have necessary equipment at hand to facilitate best patient care and save health care workers time. This invention will also decrease the risk of catheter related blood stream infections and other associated infections by facilitating best practice for patient care in regards to infusion. It provides, at arm's length, items required to perform safe and proficient patient care while fulfilling regulatory requirements. In addition, the invention assists health care personnel with time management and improves their job satisfaction and performance.

In an embodiment, the caddy attaches to the IV pole and comprises a storage container comprising a locking compartment for pre-filled syringes, an open tray for hub cleansing swabs and other medical supplies, and a clamp configured to attach the storage container to the IV pole. The syringes may be filled with saline, heparin, or other patient prescribed medications/solutions required by the FDA to be secured when not in use.

In an embodiment, the invention comprises a caddy comprising a non-permeable plastic locking box which attaches to an IV pole or bedside bar in a medical setting using a clamp. The caddy comprises a locking compartment that locks to store IV flush syringes and also comprises an open tray to hold swabs for IV line hub or lumen cleansing.

In an embodiment, the caddy comprises a storage container comprising a locking compartment for FDA-required medications to be stored, a second compartment to store items used to assure compliance for cleansing the end caps of VAD's, and a clamp configured to attach to the IV pole directly beside the patient. It will go wherever the patient goes, so items are at hand for best and expedient patient care while fulfilling agency requirements. In an embodiment, the locking compartment holds prefilled syringes containing solutions used for flushing IV lines and other equipment. These solutions are considered medications by the FDA and must be locked unless in use. In at least one embodiment, the pre-filled syringes contain a solution comprising saline. In at least one embodiment, the pre-filled syringes contain a solution comprising heparin. In at least one embodiment, the pre-filled syringes contain a solution comprising narcan.

In at least one embodiment, the invention is a bedside caddy for storing medical supplies comprising a storage container and a clamp configured to attach the storage container to an IV pole wherein the storage container comprises a locking compartment and an open tray. In an embodiment, the open tray contains one or more cleansing swabs of alcohol. In an embodiment, the open try contains one or more cleansing swabs of chlorhexidine. In an embodiment, the open tray contains one or more cleansing swabs of povidine/iodine. In an embodiment, the open tray contains one or more cleansing swab caps.

In at least one embodiment, the invention is a bedside system for infection prevention comprising a caddy comprising a storage container and a clamp configured to attach the storage container to an IV pole wherein the storage container comprises a locking compartment and an open tray and wherein the locking compartment contains pre-filled syringes and the open tray contains cleansing swabs.

In at least one embodiment, the caddy comprises a tray on the front of the caddy to store the swabs/devices used to cleanse the VAD (Vascular Access Device) hub prior to all infusions and flushes as recommended by the following organizations:

JCAHO (Joint Commission on Accreditation of Healthcare Organizations)
CDC (Centers for Disease Control)
OSHA (Occupational Safety and Health Administration)
INS (Infusion Nurses Society)
ONS (Oncology Nursing Society)
AVA (Association for Vascular Access)
NKF (National Kidney Foundation)

The items stored can also be for other purposes such as other health care related conditions. They could be for enteral patients or even the labor force where some items must be locked per regulatory guidelines.

FIG. 1 shows a front view of one embodiment of the caddy (10) that would attach to an IV pole or other piece of bedside equipment (not shown). Prefilled syringes containing the IV flushing solutions may be stored in the locking compartment 40. The locking device 50 may be chosen from a wide variety of locks such as a numeric or a keyed lock, depending upon needs and wants of the consumer. Cleansing swabs such as alcohol or chlorhexidine swabs to cleanse the hubs on the end caps of VAD's may be stored in the open tray 70 attached at the front bottom of the caddy. After unlocking the locking device, the pre-filled syringes can be accessed by lifting the lid 80 which is attached to the locking compartment by the lid hinges 90. The hinges and lid can be attached in different ways to the locking compartment to allow the lid to open in different directions (upwards, downwards, side-to-side, radially, etc.). For the embodiment shown in FIG. 1, the hinges are attached to the lid and locking compartment to allow the lid to open in an upward fashion. The lid may comprise a knob or handle for easier lifting, or a groove or tab. The caddy attaches to the IV pole using a clamp device (15) which enables the IV Pole flush and swab caddy to attach to an IV pole or any pole to make items convenient for staff to administer best patient care. The caddy can be attached to an IV pole or any other pole by loosening the C-clamp device and then placing the C-clamp around the pole and then tightening the screw to the pole creating a tension fitting to hold the caddy in place.

Figure 2:
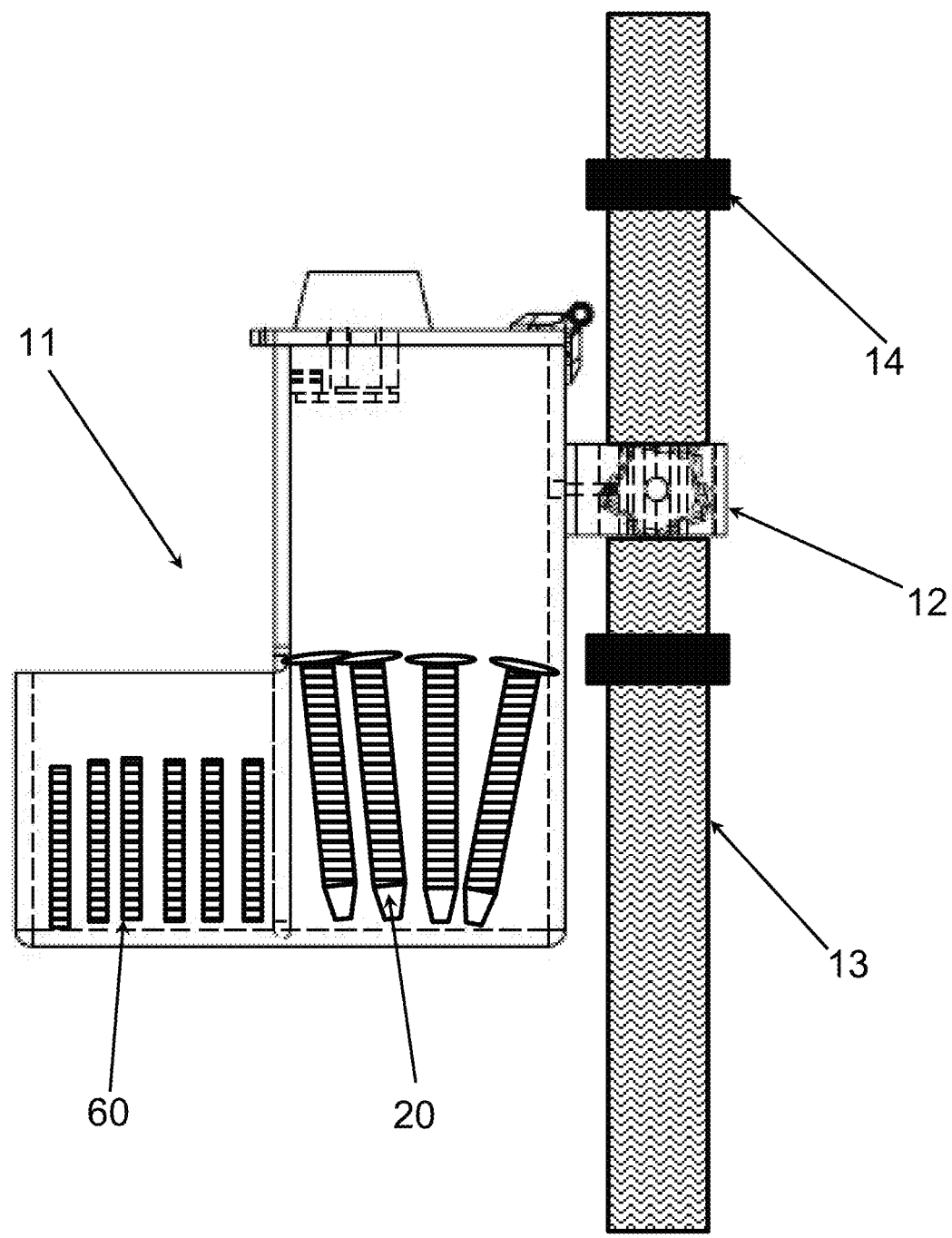
FIG. 2 is a side view of one embodiment of the invention showing an attachment to an IV pole.

FIG. 2 shows the side view of the caddy 11 showing how the clamp 12 attaches to any pole or other piece of bedside equipment 13. It could also attach to other non-round objects as necessary. Optional locking devices 14 can be used to prevent theft or unauthorized removal of the caddy from the IV pole or other piece of bedside equipment. Pre-filled syringes 20 are stored in the locking compartment. Cleansing swabs 60 and other medical supplies are stored in the open tray.

The clamp can be a C-clamp, ring clamp, or any other suitable clamp design for attaching the caddy to an IV pole or other piece of bedside equipment. Suitable clamps and other devices for attaching the caddy to an IV pole or other piece of bedside equipment can be found in US Patent Application #2011002195, filed Jul. 13, 2010, which is incorporated by reference in its entirety.

The location of the open tray relative to the locking compartment can vary depending on the design preferred for patient care or facility preference. In at least one embodiment, the entire open tray is located below the locking compartment. In an embodiment, the opening of the open tray is below the opening of the locking compartment. In at least one embodiment, the open tray is located above the locking compartment. In at least one embodiment, the open tray is located adjacent to the locking compartment. In at least one embodiment, the caddy comprises a plurality of locking compartments. In at least one embodiment, the caddy comprises a plurality of open trays.

The location of the locking device and the locking device mechanism can be varied. In at least one embodiment, the locking device is on the front of the caddy. In at least one embodiment, the locking device is on the lid of the locking compartment. In at least one embodiment, the locking device is on the side of the caddy closest to the patient. In at least one embodiment, the locking device is on the side of the caddy furthest from the patient. The locking device can be a mechanical lock. In at least one embodiment, the locking device uses a combination lock. In at least one embodiment the locking device uses a keyed lock. In at least one embodiment, the locking device uses an electronic lock. These devices and mechanisms can also be used for the optional locking device shown in FIG. 2.

The caddy can be manufactured using any suitable manufacturing method. Individual plastic pieces can be machined and then adhered together using adhesives or welding methods. The compartments can also be machined from a single block of plastic and the plastic lid with hinges can be attached. One or more components can be injection-molded. In at least one embodiment, the caddy comprises components of the clamp and components of the locking compartment that are injection molded as a single piece.

The caddy can be manufactured into different shapes depending on the space and design needs for the patient care environment as well as the manufacturing process used. The possible shapes of the caddy can include rectangular, square, oval, cylindrical, curvilinear, or racetrack. In at least one embodiment, the caddy can be manufactured in other colors, clear or opaque, depending upon facility/consumer preference In at least one embodiment, the caddy comprises components made of a non-permeable plastic wherein the components of the caddy are adhered, attached, or bonded together in a permanent fashion to allow integrity and safety. These components can include the plastic pieces that form the outer walls of the caddy as well as the walls of the locking compartments and open trays. The locking device and the clamp device can be attached, adhered, or bonded or otherwise secured to the plastic components of the caddy.

The locking compartment can be sized to fit a single day to multiple days of required stock supply for the flushes, depending on how often the patient's Vascular Access Device is flushed, or other facility requirements. In at least one embodiment, the locking compartment has a length of about 6 inches, a height of about 6 inches, and a depth of about 3 inches. In at least one embodiment, the locking compartment has a length between 3 and 10 inches, a height between 3 and 10 inches, and a depth between 1 and 6 inches. In at least one embodiment, the locking compartment is sized to contain no less than five syringes prefilled with either saline or heparin solutions. In at least one embodiment, the locking compartment is sized to contain no more than ten syringes prefilled with either saline or heparin solutions. In at least one embodiment the volume of the syringes is no less than 5 cubic centimeters, preferably no less than 10 cubic centimeters. In at least one embodiment, the syringe volume is between 5 and 20 cubic centimeters, preferably between 10 and 15 cubic centimeters, most preferably between 10 and 12 cubic centimeters. In at least one embodiment, the syringes contain no less than 5 cubic centimeters of solution. In at least one embodiment the syringes contain no less than 10 cubic centimeters of solution. In at least one embodiment, the syringes contain no more than 20 cubic centimeters of solution. The concentration of the heparin solution can vary, depending upon patient needs. In at least one embodiment, the concentration of the heparin solution is between 10 u/mL and 1000 u/mL. In at least one embodiment, the heparin solution is stored in a vial in the locking compartment. In at least one embodiment, the locking compartment is stocked daily with pre-filled syringes.

In a preferred embodiment, the locking compartment stores saline, but in other embodiments, the locking compartment could store any medication that the patient needs. Medications such as saline and heparin would not need to be labeled with the patient's name as they are considered a stock item, but still require secure storage when not in use. Other medications such as Narcan, may be labeled per patient in case IV poles were switched, or if the IV pole was not with the patient. Other medications that could be stored in the locking compartment include prescription topical or enteral medications for patients using enteral feedings. The policy has usually been determined by facility staff. Saline and heparin are usually ordered per protocol/standing order for Vascular Access Devices.

The open tray can be sized to fit a single day to multiple days of required stock supply for the cleaning swabs and other supplies needed for the flushes, depending on how often the patient's Vascular Access Device is flushed, or other facility requirements. In at least one embodiment, the open tray has a length of about 6 inches, a height of about 3 inches, and a depth of about 3 inches. In at least one embodiment, the open tray has a length between 3 and 10 inches, a height between 1 and 10 inches, and a depth between 1 and 6 inches. In at least one embodiment, the open tray contains items used for cleansing the end of the injection cap/hub. Such items include alcohol preps, chlorhexidine preps, swab caps. In at least one embodiment, other items including tape, pens, or labels are stored in the open tray. In at least one embodiment, the open tray is sized to contain no less than 5 cleaning swabs. In at least one embodiment, the open tray is sized to contain no more than ten cleaning swabs. In at least one embodiment, the open tray is sized to hold no more than 20 cleaning swabs. In at least one embodiment, the open tray is stocked daily with a supply of cleaning swabs.

The invention can also provide a bedside system for infection prevention comprising a vascular access device and a caddy wherein the caddy comprises a storage container and a clamp configured to attach the storage container to an IV pole wherein the storage container comprises a locking compartment and an open tray and wherein the locking compartment contains pre-filled syringes comprising saline, heparin, or other medication solutions and the open tray contains cleansing swabs or other medical supplies. A reminder message or instructions can also be displayed on the caddy. In at least one embodiment, at least one surface of the open tray is used to display a reminder message or instruction. An example of such a reminder includes, "Scrub the Hub for 10-15 seconds" or simply "Scrub the Hub". In at least one embodiment, the bedside caddy can have a reminder etched onto the front of the open tray stating "scrub the hub for 15 seconds every time" to assist with clinician compliance and patient education. In an embodiment, the message is displayed on the locking compartment of the caddy.

The message can be displayed in different ways, such as etching the message into the surface or applying a label with the message to the surface. In an embodiment, the message is on a card that is attached to the caddy using a clip or other methods of attachment. Other reminders, instructions, and other messages can be displayed on the caddy as facilities require or recommend.

In a preferred embodiment, the caddy comprises a nonpermeable plastic that can be cleansed per facility/customer infection control policies, more preferably the caddy comprises a clear or non-opaque plastic.

Thermoplastic polymers that can be used as the materials for this invention include polyolefins, e.g. polyethylene, polypropylene, polybutylene, and copolymers thereof, polytetrafluoroethylene, polyesters, e.g. polyethylene terephthalate, polyvinyl acetate, polyvinyl chloride acetate, polyvinyl butyral, acrylic resins, e.g. polyacrylate, and polymethylacrylate, polymethylmethacrylate, polyamides, namely nylon, polyvinyl chloride, polyvinylidene chloride, polystyrene, polyvinyl alcohol, polyurethanes, copolymers of any of the above materials, e.g. ethylene-vinyl acetate copolymers, ethylene-acrylic acid copolymers, styrene-butadiene block copolymers, Kraton rubbers and the like.

Polymer materials that can be used in the polymeric compositions of the invention include both addition polymer and condensation polymer materials such as polyolefin, polyacetal, polyamide, polyester, cellulose ether and ester, polyalkylene sulfide, polyarylene oxide, polysulfone, modified polysulfone polymers and mixtures thereof. Preferred materials that fall within these generic classes include polyethylene, polypropylene, poly(vinylchloride), polymethylmethacrylate (and other acrylic resins), polystyrene, and copolymers thereof (including ABA type block copolymers), poly(vinylidene fluoride), poly(vinylidene chloride), polyvinylalcohol in various degrees of hydrolysis (87% to 99.5%) in crosslinked and non-crosslinked forms.

Block copolymers are also useful in the process of this invention. One example is a ABA (styrene-EP-styrene) or AB (styrene-EP) polymer. Examples of such block copolymers are Kraton® type of styrene-b-butadiene and styrene-b-hydrogenated butadiene(ethylene propylene), Pebax® type of e-caprolactam-b-ethylene oxide, Sympatex® polyester-b-ethylene oxide and polyurethanes of ethylene oxide and isocyanates.

In a patient care setting, the caddy can be used by specified personnel. Specified personnel can be given or allowed to set the code on the locking device, or given a key, depending on the locking mechanism. By unlocking the device, the lid can be opened, and items such as the prefilled syringes which can be locked for safety and regulatory standards can be placed inside the locking compartment and then re-locked. Specified staff can access those items as necessary. Specified personnel can stock the cleansing swabs or other medical supplies in the open front tray for easy access to facilitate patient care. The open tray can be used such that any item that is required to be locked up for safety or per regulatory requirements is not placed therein. Material Safety Data Sheets (MSDS) sheets can be available for all items for patient safety. In at least one embodiment, the caddy includes a compartment for storing MSDS sheets.

In at least one embodiment, the following steps are used with this system:
   a. Attach the caddy to the patient's IV pole or other bedside equipment
   b. Stock the pre-filled syringes containing the infusion medications in the locking compartment (s) (saline, heparin, narcan, etc.)
   c. Close the lid to locking compartment(s) and lock the compartment(s).
   d. Stock the alcohol preps, chlorhexidine preps or swab caps in the open tray(s)
   e. To access the patient's Vascular access device (PIV, Midline, PICC, CVC, Dialysis CVC, PAC, etc.):
      i. Unlock the locking device to open the locking compartment, and obtain pre-filled syringes containing the infusion medication(s)
      ii. Take cleansing swabs for cleansing the end cap of the patients IV access device from the trays
      iii. Re-lock the locking compartment.
      iv. Perform patient care per policy
         1. Do not re-enter locking compartment with soiled hands or place soiled or used equipment back into caddy.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

I claim:

1. A bedside system for infection prevention comprising a vascular access device and a caddy wherein the caddy comprises a storage container and a clamp configured to attach the storage container to an IV pole wherein the storage container comprises a locking compartment and an open tray and wherein the locking compartment contains pre-filled syringes comprising saline solution and the open tray contains cleansing swabs comprising alcohol.

2. The bedside system of claim 1 wherein at least one surface of the open tray comprises a printed message.

3. The bedside system of claim 2 wherein the printed message is etched into the surface of the open tray.

4. The bedside system of claim 2 wherein the printed message is on a label or card attached to the open tray.

5. The bedside system of claim 1 wherein the locking compartment stores no more than five pre-filled syringes.

6. The bedside system of claim 1 wherein the open tray stores no more than twenty cleansing swabs.

7. The bedside system of claim 1 wherein the locking compartment further comprises a keyed or combination lock attached to the lid of the locking compartment.

8. The bedside system of claim 1 wherein the clamp is also secured to the IV pole by a lock.

* * * * *